United States Patent [19]
Stiefel et al.

[11] Patent Number: 5,466,446
[45] Date of Patent: Nov. 14, 1995

[54] TOPICAL COMPOSITIONS CONTAINING BENSOYL PEROXIDE AND CLINDAMYCIN AND METHOD OF USE THEREOF

[75] Inventors: Werner K. Stiefel, Coral Gables, Fla.; Karl F. Popp, Schodack Landing, N.Y.

[73] Assignee: Stiefel Laboratories, Inc., Coral Gables, Fla.

[21] Appl. No.: 197,076

[22] Filed: Feb. 16, 1994

[51] Int. Cl.⁶ .................... A61K 31/70; A61K 31/74; A61K 31/78; A61K 31/075
[52] U.S. Cl. .................... 424/78.37; 514/29; 514/714; 514/859; 514/864
[58] Field of Search .................... 424/62; 514/859

[56] References Cited

U.S. PATENT DOCUMENTS

| | | | |
|---|---|---|---|
| 4,056,611 | 11/1977 | Young | 424/62 |
| 4,387,107 | 6/1983 | Klein et al. | 424/62 |
| 4,497,794 | 2/1985 | Klein et al. | 424/81 |
| 4,671,956 | 6/1987 | Bouillon et al. | 424/59 |
| 4,692,329 | 9/1987 | Klein et al. | 424/81 |

FOREIGN PATENT DOCUMENTS

| | | | |
|---|---|---|---|
| 2378523 | 1/1977 | France | 424/62 |
| US93/00464 | 1/1993 | WIPO | 424/62 |
| US93/03325 | 4/1993 | WIPO | 424/62 |

OTHER PUBLICATIONS

Eady et al., "The Use of Antibiotics in Acne Therapy: oral or topical administration?", *Journal of Antimicrobial Chemotherapy*, vol. 10, pp. 89–115 (1982).

Eady et al., "Should Topical Antibiotics be Used for the Treatment of Acne Vulgaris?", *British Journal of Dermatology*, vol. 107, pp. 235–146 (1982).

Leydon et al., "Topical Antibiotics and Topical Antimicrobial Agents in Acne Therapy", *Acta Dermatovener* (Stockholm), Suppl. 89, pp. 75–82 (1980).

Migdon, et al., "A Stability Study of Clindamycin Hydrochloride and Phosphate Salts in Topical Formulations", *Drug Development and Industrial Pharmacy*, vol. 10(4), pp. 563–573 (1984).

Milstone, et al., "Pseudomembranous Colitis After Topical Application of Clindamycin", *Arch Dermatol*, vol. 117, pp. 154–155 (1981).

Tucker, et al., "Comparison of Topical Clindamycin Phosphate, Benzoyl Peroxide, and a Combination of the Two for the Treatment of Acne vulgaris" *British Journal of Dermatology*, vol. 110, pp. 487–492 (1984).

*Primary Examiner*—Dale R. Ore
*Attorney, Agent, or Firm*—Mathews, Woodbridge & Collins

[57] ABSTRACT

Dermatological conditions are treated by topically applying to the affected area an effective amount of a combination benzoyl peroxide and clindamycin composition.

2 Claims, No Drawings

TOPICAL COMPOSITIONS CONTAINING BENSOYL PEROXIDE AND CLINDAMYCIN AND METHOD OF USE THEREOF

BACKGROUND OF THE INVENTION

The present invention pertains to topical preparations comprising benzoyl peroxide and clindamycin, which are used for treating skin disorders involving the sebaceous glands and follicles in humans.

Skin disorders involving the sebaceous glands and follicles in humans include conditions such as acne and rosacea, as well as other noninfectious dermatological diseases involving microorganisms. Such disorders are often marked by inflammation.

In the past, these dermatological disorders have been treated with oral and/or topical antibacterial agents. The oral antibiotics used include tetracycline, erythromycin and minocycline. The topical compositions used have separately contained the antibiotics tetracycline, erythromycin and clindamycin, as well as benzoyl peroxide, which exerts its antibacterial action via its potent oxidizing properties. However, it is the strong oxidizing properties of peroxide that results in unstable compositions. Benzoyl peroxide also can act as a sebosuppressant, an irritant, and comedolytic agent.

Topical compositions which combine at least two active antibacterial agents have been proposed as a treatment to these disorders. These compositions require compounding by the pharmacist and must be refrigerated. After three months of refrigeration, the compositions lose potency and effectiveness and must be replaced with a new batch.

For example, a currently-available combination product, Benzamycin®, is a topical gel containing 3% of erythromycin and 5% of benzoyl peroxide. Benzamycin®, however, has several drawbacks. First, the product is supplied to pharmacies as a benzoyl peroxide gel in a first container and erythromycin powder in a second container. The product thus requires compounding by the pharmacist, who must (1) dissolve the erythromycin in alcohol, (2) add the erythromycin solution to the gel, and (3) stir until homogeneous in appearance. Second, the alcohol present in the composition as dispensed amounts to 16% of the total composition, which often proves to be excessively drying and irritating to the skin, particularly in combination with the benzoyl peroxide. Third, the composition as dispensed by the pharmacist (i.e., after reconstitution or compounding) lacks the stability necessary for extended storage at room temperature. The combination product can be stored under refrigeration for up to three (3) months.

Other efforts at improving the stability of combination products in particular have relied on the use of novel packaging which keeps the active agents separated to maintain stability until the time of use. However, compounding is still necessary at the time of dispensing and stability remains a problem, because the product must be used immediately upon being prepared.

SUMMARY OF THE INVENTION

The present invention pertains to topical compositions comprising the combination of benzoyl peroxide and clindamycin admixed with a topically acceptable pharmaceutical carrier.

In particular, the compositions comprise an effective amount of a mixture of (i) benzoyl peroxide, (ii) clindamycin, and (iii) a topically acceptable pharmaceutical carrier.

The compositions do not require compounding at the time of dispensing and maintain stability indefinitely depending on the storage temperature, despite the relative incompatibility of benzoyl peroxide and clindamycin.

This invention also relates to methods for treating skin disorders involving the sebaceous glands and follicles in humans which comprises topically applying an effective amount of a mixture of benzoyl peroxide and clindamycin to the affected area.

The present invention provides for combination topical preparations which maintain stability and effectiveness for at least 3 to 18 months at ambient or room temperature. It has been found that the greater the amount of clindamycin in the final product, the greater the stability is maintained. Stability is maintained indefinitely under refrigeration because degradation is slowed through the storage temperature. This improved stability provides pharmacists and other dispensers of medication with a product which no longer requires compounding at the time of dispensing. Because compounding is no longer required, homogenity is controlled at the point of manufacture, which improves dosing and ultimately compliance. Furthermore, the present invention does not employ alcohol as a diluent, which eliminates the drying or irritating effects commonly associated therewith.

DESCRIPTION OF THE PREFERRED EMBODIMENT

The topical compositions and methods of the present invention utilize an effective amount of a mixture of benzoyl peroxide and clindamycin. The benzoyl peroxide and clindamycin components no longer need to be separately maintained, but are combined, along with a pharmaceutical carrier, to form the composition.

An effective amount of a mixture of benzoyl peroxide and clindamycin is any amount which produces the desired results. Generally an effective amount is from about 4.5% to about 11% by weight of the total composition of benzoyl peroxide and from about 0.90% to about 2.5% by weight of the total composition of clindamycin. However, the effective amount can encompass a nominal 11% by weight of benzoyl peroxide and 1% by weight of clindamycin of the total composition.

In particular, the ratio of benzoyl peroxide to clindamycin is from about 1.8:1 to 12:1. Particularly preferred are compositions wherein the ratio of benzoyl peroxide to clindamycin is from about 4:1 to about 5:1.

In addition, a suitable pharmaceutical carrier is employed. Suitable topically acceptable pharmaceutical carriers are those which typically are used in the topical application of pharmaceuticals and cosmetics. Examples of such carriers include solutions, lotions, creams, ointments and gels.

The benzoyl peroxide and clindamycin are mixed, either separately or together, with the inert ingredients which form the pharmaceutical carrier. In a final composition, the benzoyl peroxide will be present in an amount of from about 4.5 to about 11% while the clindamycin will be present in an amount of from about 0.90 to 2.5% of the overall composition. The precise amount of inert ingredients added will depend on the amounts of benzoyl peroxide and clindamycin used to make the final product.

Referring to the formulation of the compound, a gel is initially formed. The gel is composed of a carbomer, Disodium Monolaurel Sulfosuccinate, and disodium EDTA to which methylparaben is added as a preservative. Purified water is used as a diluent.

After the gel is formed, wetting agents and emollients are added. After the pH is adjusted, the active ingredients are added to form the final compound.

As discussed above, the active ingredients can be added to the inert ingredients at the same time or separately.

The resultant combination maintains stability for a minimum of three months at room temperature and relative humidity.

Stability of the compound is maintained for longer periods of time depending on the amount of clindamycin employed in the final product and the ratio of benzoyl peroxide to clindamycin. For example, when 1.2% of clindamycin is present in the compound, the shelf life can reach from seven to fourteen months at room temperature while maintaining effectiveness. In contrast, when only 1.02% of clindamycin is employed, the shelf life of the product is about twelve weeks.

Differences in packaging components and manufacturing techniques yield varied formula responses over a period ranging between seven and fourteen months in stability testing as evidenced by the following data:

| Ref. No. | BPO/Clindamycin Ratio | Minimum Projected Stability |
|---|---|---|
| A | 5/1.2 | 14 months |
| B | 5/1.2 | 9 months |
| C | 5/1.2 | 7 months |
| D | 5.9/1 | 7 months |
| E | 5/1.02 | 3 months |
| F | 5/1.02 | 3 months |

In addition to the amount of clindamycin as a control over degradation, the temperature at which the composition is stored determines the length of time that the composition remains stable. When the composition is stored at a temperature below ambient temperature (25° C.), the stability is maintained indefinitely. For example, storing the compound at 6° C. with the proper amount of overage of clindamycin results in an anticipated shelf life of 3 to 5 years.

Advantageously, the final product requires no compounding by the pharmacist. In addition, compliance with exact amounts is possible with a lessened chance of impurities entering the product and contaminating it.

The compositions according to the present invention generally are topically applied to the affected skin once or twice daily. However, since the compositions of the present invention typically are used under a physician's care, the precise treatment regimen in each case will be determined by the physician based upon the exact diagnosis, the severity of the condition, concurrent use of other therapeutic agents, responsiveness to treatment, tolerance of treatment, and other related medical considerations.

The following examples will serve to further typify the nature of the invention but should not be construed as a limitation on the scope thereof, which is defined solely by the appended claims. In the examples, the following inert ingredients are used: Carbopol 940, known in the art as carbomer; Monamate LA-100, known in the art as Disodium Monolaurel Sulfosuccinate; Pluracare L-62, known in the art as Poloxamer 182; Dow Fluid 200, known in the art as dimethicone; Hampene Na$_2$, known in the art as disodium EDTA; and Syloid 244 FP, known in the art as hydrated silica.

EXAMPLE 1

A highly stable gel composition is prepared using the following components. The active ingredients are benzoyl peroxide and clindamycin phosphate. The remaining components are inert or auxiliary.

| Ingredient | Parts by Weight |
|---|---|
| Gel: | |
| Purified Water | 86.50% |
| Carbopol 940 | 2.00% |
| Monamate LA-100 | 0.04% |
| Hampene Na$_2$ | 0.10% |
| Methylparaben | 0.30% |
| Total: | 88.94% |

The gel is combined with the following to produce the compound:

| | |
|---|---|
| Wetting Agents and Emollients: | |
| Pluracare L-62 | 0.20% |
| Glycerin | 4.00% |
| Dow Fluid 200 | 0.10% |
| Syloid 244 FP | 0.25% |
| Total: | 4.55% |
| pH Adjustment: | |
| Sodium Hydroxide | 0.31% |
| Total: | 0.31% |
| Active Ingredients: | |
| Benzoyl Peroxide | 5.00% |
| Clindamycin Phosphate | 1.20% |
| Total: | 6.20% |
| Total for composition: | 100.00% |

EXAMPLE 2

The following composition is obtained when the following component formulations are mixed in equal parts, and later combined to yield the highly stable product.

| Benzoyl peroxide formulation | |
|---|---|
| Ingredient | Parts by Weight |
| Gel: | |
| Purified Water | 82.70% |
| Carbopol 940 | 2.00% |
| Monamate LA-100 | 0.04% |
| Hampene Na$_2$ | 0.10% |
| Methylparaben | 0.30% |
| Total: | 85.14% |

The gel is combined with the following to produce the compound:

| Wetting Agents and Emollients: | |
|---|---|
| Pluracare L-62 | 0.20% |
| Glycerin | 4.00% |
| Dow Fluid 200 | 0.10% |
| Syloid 244 FP | 0.25% |
| Total: | 4.55% |
| pH Adjustment: | |
| Sodium Hydroxide | 0.31% |
| Total: | 0.31% |
| Active Ingredients: | |
| Benzoyl Peroxide | 10.00% |
| Clindamycin Phosphate | — |
| Total: | 10.00% |
| Total for composition: | 100.00% |

Clindamycin formulation

| Gel: | |
|---|---|
| Purified Water | 90.30% |
| Carbopol 940 | 2.00% |
| Monamate LA-100 | 0.04% |
| Hampene Na$_2$ | 0.10% |
| Methylparaben | 0.30% |
| Total: | 92.74% |

The gel is combined with the following to produce the compound:

| Wetting Agents and Emollients: | |
|---|---|
| Pluracare L-62 | 0.20% |
| Glycerin | 4.00% |
| Dow Fluid 200 | 0.10% |
| Syloid 244 FP | 0.25% |
| Total: | 4.55% |
| pH Adjustment: | |
| Sodium Hydroxide | 0.31% |
| Total: | 0.31% |
| Active Ingredients: | |
| Benzoyl Peroxide | — |
| Clindamycin Phosphate | 2.40% |
| Total: | 2.40% |
| Total for composition: | 100.00 |

The resultant mixture is essentially 10% of benzoyl peroxide with essentially 2% clindamycin.

EXAMPLE 3

Tables 1 and 2 show the stability of the active ingredients. A fourteen-month analysis was performed on a 5.9% benzoyl peroxide and 1% clindamycin gel formulation. Measurements were taken at the end of 3 months and every month thereafter until the 8th month. No measurements were taken at 8 months. Thereafter, measurements were taken at 9, 12, and 14 months. The composition was stored at 3 different temperatures, i.e., 6° C., 25° C., and 30° C. The level of clindamycin was measured at each temperature, as well as the amount of benzoyl peroxide. The results are as follows:

TABLE 1

Benzoyl Peroxide 5% (5.9% in formula) and Clindamycin 1% (1% in formula) Clindamycin (as % w/w)

| | 6° C. | 25° C. | 30° C. |
|---|---|---|---|
| Initial | | 1.01 | |
| 3 months | 0.95 | 0.90 | 0.77 |
| 4 months | 1.01 | 0.95 | 0.79 |
| 5 months | 1.04 | 0.95 | 0.79 |
| 6 months | 0.96 | 0.91 | 0.71 |
| 7 months | 1.05 | 0.92 | 0.70 |
| 9 months | 1.03 | ND | ND |
| 12 months | 0.98 | 0.79 | 0.37 |
| 14 months | 0.98 | 0.76 | 0.27 |

ND = No Data

TABLE 2

Benzoyl Peroxide [BPO] (as % w/w)

| | 6° C. BPO | 25° C. BPO | 30° C. BPO |
|---|---|---|---|
| Initial | | 6.13 | |
| 3 months | 5.97 | 5.90 | 5.98 |
| 4 months | 6.07 | 6.05 | 5.98 |
| 5 months | 6.08 | 5.96 | 5.84 |
| 6 months | 6.13 | 6.04 | 5.91 |
| 7 months | 6.23 | 6.19 | 6.06 |
| 9 months | 6.02 | 5.95 | |
| 12 months | 5.95 | 5.89 | 5.63 |
| 14 months | 6.10 | 6.10 | 5.77 |

EXAMPLE 4

Tables 3 and 4 show the stability of the active ingredients in the composition containing 5% of benzoyl peroxide and 1.2% of clindamycin.

A six-month analysis of the composition was undertaken following the procedure of Example 3 and utilizing a different amount of clindamycin and benzoyl peroxide.

TABLE 3

Benzoyl Peroxide 5% [BPO] (5% in formula) and Clindamycin 1% (1.2% in formula) Clindamycin (as % w/w)

| | 6° C. | 25° C. | 30° C. |
|---|---|---|---|
| Initial | | 1.24 | |
| 1 months | 1.25 | 1.24 | 1.15 |
| 2 months | 1.28 | 1.21 | 1.01 |
| 3 months | 1.23 | 1.13 | 0.94 |
| 6 months | 1.21 | 1.05 | ND |

TABLE 4

Benzoyl Peroxide [BPO] (as % w/w)

| | BPO | BPO | BPO |
|---|---|---|---|
| Initial | | 5.09 | |
| 1 month | 5.10 | 5.02 | 5.08 |
| 2 months | 5.25 | 5.20 | 5.13 |
| 3 months | 5.16 | 5.18 | 4.82 |
| 6 months | 5.07 | 5.06 | ND |

ND = No Data

What is claimed is:
1. A topical gel composition for treating skin disorders involving the sebaceous glands and follicles in humans, said composition consisting essentially of an effective amount of a mixture of: (i) at least 4.5% by weight of benzoyl peroxide, and (ii) at least 0.9% by weight of clindamycin, admixed with a topically acceptable pharmaceutical carrier consisting essentially of about 0.04% disodium monolaurel sulfosuccinate, about 2.0% of a carbomer, about 0.1% of disodium ethylene diaminetetraacetic acid, about 0.1% of dimethicone, about 0.25% of hydrated silica, about 0.20% of poloxamer 182 and about 0.31% of sodium hydroxide by weight of said composition, wherein the composition is stable for at least 3 months at ambient temperature.

2. A method for treating skin disorders involving the sebaceous glands and follicles in humans which consists essentially of topically applying to affected skin an effective amount of a mixture of at least 4.5% by weight of benzoyl peroxide and at least 0.9% by weight of clindamycin admixed with a topically acceptable pharmaceutical carrier in gel form, consisting essentially of about 0.04% disodium monolaurel sulfosuccinate, about 2.0% of a carbomer, about 0.1% of disodium ethylene diaminetetraacetic acid, about 0.1% of dimethicone, about 0.25% of hydrated silica, about 0.20% of poloxamer 182 and about 0.31% of sodium hydroxide by weight of said composition.

* * * * *

UNITED STATES PATENT AND TRADEMARK OFFICE
CERTIFICATE OF CORRECTION

PATENT NO. : 5,466,446
DATED : NOVEMBER 14, 1995
INVENTOR(S) : WERNER K. STIEFEL and KARL F. POPP It is certified that error appears in the above-indentified patent and that said Letters Patent is hereby corrected as shown below:

ON THE TITLE PAGE: Item [54] and Column 1, line 1;

Change "BENSOYL" to —BENZOYL—.

In column 2, line 65, change "Monolaurel" to —Monolauryl—.

In column 3, line 64, change "Monolaurel" to —Monolauryl—.

In column 7, line 6, change "Monolaurel" to —Monolauryl—.

In column 8, line 7, change "Monolaurel" to —Monolauryl—.

Signed and Sealed this

Eleventh Day of June, 1996

Attest:

BRUCE LEHMAN

Attesting Officer

Commissioner of Patents and Trademarks